US009662183B2

United States Patent
Lowe et al.

(10) Patent No.: US 9,662,183 B2
(45) Date of Patent: May 30, 2017

(54) ELECTRO-ORTHODONTIC DEVICE

(71) Applicant: OrthoAccel Technologies Inc., Bellaire, TX (US)

(72) Inventors: Michael K. Lowe, Bellaire, TX (US); Lawrence W. Swol, Bellaire, TX (US)

(73) Assignee: OrthoAccel Technologies, Inc., Bellaire, TX (US)

(*) Notice: Subject to any disclaimer, the term of this patent is extended or adjusted under 35 U.S.C. 154(b) by 299 days.

(21) Appl. No.: 13/943,651

(22) Filed: Jul. 16, 2013

(65) Prior Publication Data

US 2014/0023983 A1    Jan. 23, 2014

Related U.S. Application Data

(60) Provisional application No. 61/673,236, filed on Jul. 18, 2012.

(51) Int. Cl.
*A61C 7/00* (2006.01)
*A61C 7/08* (2006.01)
*A61C 7/36* (2006.01)

(52) U.S. Cl.
CPC ............ *A61C 7/006* (2013.01); *A61C 7/008* (2013.01); *A61C 7/08* (2013.01); *A61C 7/36* (2013.01)

(58) Field of Classification Search
CPC .......... A61C 7/08; A61C 7/006; A61C 7/008; A61C 7/36
USPC .................................................. 433/18, 24
See application file for complete search history.

(56) References Cited

U.S. PATENT DOCUMENTS

| | | | |
|---|---|---|---|
| 4,153,060 A * | 5/1979 | Korostoff | A61C 7/00 433/215 |
| 4,519,779 A * | 5/1985 | Lieb | A61C 7/00 433/18 |
| 4,854,865 A * | 8/1989 | Beard | A61C 7/00 433/18 |
| 5,554,971 A | 9/1996 | Foster | |
| 5,780,958 A | 7/1998 | Strugach | |
| 6,102,705 A * | 8/2000 | Darnell | 433/216 |
| 6,648,639 B2 | 11/2003 | Mao | |
| 6,832,912 B2 | 12/2004 | Mao | |
| 6,984,128 B2 * | 1/2006 | Breining | A61C 7/00 433/24 |
| 7,029,276 B2 | 4/2006 | Mao | |
| 8,500,446 B2 * | 8/2013 | Lowe | 433/18 |
| 2001/0012608 A1 * | 8/2001 | Darnell | 433/216 |
| 2001/0038993 A1 * | 11/2001 | Lindquist | 433/37 |

(Continued)

FOREIGN PATENT DOCUMENTS

| WO | 0178217 | 10/2001 |
|---|---|---|
| WO | 2013155366 | 10/2013 |

OTHER PUBLICATIONS

Kau, et al., The clinical evaluation of a novel cyclical force generating device in orthodontics, Orthodontic Practice 1(1) (2010).

(Continued)

*Primary Examiner* — Cris L Rodriguez
*Assistant Examiner* — Hao D Mai
(74) *Attorney, Agent, or Firm* — Boulware & Valoir (57) ABSTRACT

An electro-orthodontic appliance is provided that helps accelerate orthodontic tooth movement through the application of a controlled electrical current to gum and teeth, thus stimulating osteogenesis.

12 Claims, 7 Drawing Sheets

(56) References Cited

U.S. PATENT DOCUMENTS

| | | |
|---|---|---|
| 2007/0103016 A1 | 5/2007 | Park |
| 2008/0129130 A1 | 6/2008 | Mun |
| 2008/0227046 A1 | 9/2008 | Lowe |
| 2008/0227047 A1 | 9/2008 | Lowe |
| 2008/0233541 A1* | 9/2008 | De Vreese et al. ............ 433/216 |
| 2009/0051312 A1 | 2/2009 | Simon |
| 2009/0117513 A1* | 5/2009 | Nemeh ................ A61C 19/063 433/32 |
| 2009/0224616 A1 | 9/2009 | An |
| 2010/0055634 A1 | 3/2010 | Spaulding |
| 2010/0082027 A1 | 4/2010 | Chalmers |
| 2010/0092916 A1* | 4/2010 | Teixeira ................ A61H 23/02 433/103 |
| 2010/0151426 A1* | 6/2010 | Tachi ........................ G08B 6/00 434/113 |
| 2010/0261133 A1* | 10/2010 | Lax ................................. 433/71 |
| 2011/0136070 A1 | 6/2011 | Rubin |
| 2012/0040300 A1* | 2/2012 | Levens et al. .................... 433/5 |
| 2012/0322018 A1 | 12/2012 | Lowe |
| 2012/0322024 A1* | 12/2012 | De Vreese et al. ............. 433/29 |
| 2013/0059263 A1 | 3/2013 | Lowe |
| 2013/0252193 A1* | 9/2013 | Bowman et al. ................. 433/6 |

OTHER PUBLICATIONS

Davidovitch Z, et al., Electric currents, bone remodeling, and orthodontic tooth movement. II. Increase in rate of tooth movement and periodontal cyclic nucleotide levels by combined force and electric current, Am J Orthod. 77(1):33-47 (1980).

Hashimoto, H., Effect of Micropulsed Electricity on Experimental Tooth Movement, Nihon Kyosei Shika Gakkai Zasshi. 49(4):352-61 (1990).

Rubin CT, Optimization of electric field parameters for the control of bone remodeling: exploitation of an indigenous mechanism for the prevention of osteopenia, J Bone Miner Res. 8 Suppl 2:S573-81 (1993).

Showkatbakhsh R., et al., The effect of pulsed electromagnetic fields on the acceleration of tooth movement, World J Orthod. 11(4):e52-6 (2010).

Stark, T.M., et al., Effect of pulsed electromagnetic fields on orthodontic tooth movement, American Journal of Orthodontics and Dentofacial Orthopedics 91(2): 91-104 (1987).

* cited by examiner

ELECTRO-ORTHODONTIC DEVICE

PRIOR RELATED APPLICATIONS

This application claims priority to 61/673,236, filed Jul. 18, 2012 and incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to devices used to speed orthodontic remodeling, in particular an electro-orthodontic device is described that stimulates orthodontic remodeling by micropulsed currents or electromagnetic fields.

BACKGROUND OF THE INVENTION

A malocclusion is a misalignment of teeth or incorrect relation between the teeth of the two dental arches. The term was coined by Edward Angle, the "father of modern orthodontics," as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom results in malocclusion.

There are three classes of malocclusions, Class I, II, and III. Further, class II is subdivided into three subtypes:

Class I: Neutrocclusion Here the molar relationship of the occlusion is normal or as described for the maxillary first molar, but the other teeth have problems like spacing, crowding, over or under eruption, etc.

Class II: Distocclusion (retrognathism, overjet) In this situation, the upper molars are placed not in the mesiobuccal groove but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II but the central incisors are retroclined and the lateral incisors are seen overlapping the central incisors.

Class III: Mesiocclusion (prognathism, negative overjet) In this case the upper molars are placed not in the mesiobuccal groove but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has a large mandible or a short maxillary bone.

Orthodontics, formerly orthodontia (from Greek orthos "straight or proper or perfect"; and odous "tooth") is that specialty of dentistry that is concerned with the study and treatment of malocclusions. Orthodontics treats malocclusion through the movement of teeth, as well as control and modification of facial growth, and occasionally in severe cases, through surgery.

Dental braces (also known as orthodontic braces, or simply braces) are commonly used to align and straighten teeth. In this approach, the braces provide a continuous static force to the teeth via an archwire connected to brackets affixed to each tooth. As the teeth slowly migrate due to the force, the force is dissipated. The archwires are then adjusted to add additional force and to continue the desired tooth movement. Although effective, this widely practiced orthodontic treatment takes about twenty-four months on average to achieve success. Furthermore, treatment time cannot be shortened by increasing the force due to pain and risk of root resorption from the excess force. The long treatment time, associated pain and the unpleasant aesthetics discourage patients from using such treatment. Indeed, some studies show that 75 percent of Americans could benefit from orthodontic treatment, yet remain untreated.

The aligner in contrast, is a clear molded device designed with the aid of computer modeling and that applies a continuous static force to the teeth. A series of aligners are designed to progressively move the teeth to a desired position. Because the device is transparent, it is more aesthetically appealing, and it is popular with teen and adult users. However, since the device can be taken off, treatment times usually are longer. It is also more limited in the classifications of malocclusion that can be addressed since force is not easily applied in all directions.

Dental researchers have long postulated that a pulsating force might be used to move teeth more rapidly and to ease the discomfort of traditional orthodontics, but Dr. Mao was probably the first to prove that cyclic forces improved and accelerated dental straightening (see U.S. Pat. No. 6,684,639, U.S. Pat. No. 6,832,912, U.S. Pat. No. 7,029,276). Certain dynamic loading patterns (cycling force with rest periods) were shown to greatly increase bone formation compared to basic dynamic loading. Inserting rest periods is now known to be especially efficacious as it allows mechano-sensitivity to be restored to the bone tissue. A point of diminishing returns is reached within each loading session. Therefore, intermittently loading cyclic force can increase the rate of bone formation significantly.

The early Mao and similar studies provided a basis for both possible efficacy and likely safety for using vibration in humans to assist orthodontic tooth movement, but the animal studies needed to be repeatable in humans, and the devices used by Mao and the others were completely unsuitable for human clinical use, involving clamping a rabbit head in a fixation device, and applied force to the cranium to assess sutural osteogenesis. Further, Mao used cyclic forces of 5 Newtons (N) and 0.2-1 Hz and such forces are probably too high for human use, both from comfort and root resorption perspectives.

OrthoAccel Technologies Inc., was the first to invent and clinically test a commercially successful dental vibrating device, as described in US2008227046 and related cases, designed to apply cyclic forces to the dentition for accelerated remodeling purposes. Both intra-oral and extra-oral embodiments are described in US2008227046, each having processors to capture and transmit patient usage information.

The bite plate was specially designed to contact occlusal as well as lingual and/or facial surfaces of the dentition, and thus was more effective than any prior art devices in conveying vibrational forces to the teeth, transmitting vibration in two axes. Further, the device was tested in clinical trials and was shown to speed orthodontic remodeling as much as 50%, and is truly a breakthrough in orthodontic technology (Kau 2010).

Finally, the device is slim, capable of hands free operation, lacks the bulky head gear of prior art devices, and has optimized force and frequency for orthodontic remodeling. Thus, its comfort level and compliance was also found to be high, with patients reporting that they liked the device, especially after the motor was redesigned to be quieter and smoother, as described in US2010055634 et seq. In fact, this device has been marketed as AcceleDent™ in the United States and several other countries and has achieved remarkable commercial success since its recent introduction. AcceleDent™ represents the first successful clinical approach to accelerate orthodontic tooth movement by modulating bone biology in a non-invasive and non-pharmacological manner.

During the 1960s, there was considerable interest in piezoelectricity as a stimulus for bone remodeling. This arose because it was noted that distortion of crystalline structures generated small electrical charges, which potentially may have been responsible for signaling bone changes associated with mechanical forces. Therefore, the interest in electricity and bone remodeling was considerable.

In 1980, Davidovitch et al. showed that cat teeth treated by force and electricity moved significantly faster than those treated by force alone. These results suggested that orthodontic tooth movement can be accelerated by the use of locally applied, small electric currents. Then in 1990, Hashimoto confirmed that cat teeth moved more rapidly under a 60 gram force combined with a one hertz square wave pulse of 6 volts, which induced a current of about 10 $\mu$Amp. However, no dedicated device was built by these researchers, who used an experimental set-up, completely inappropriate for human use.

In 1987, Stark tested a pulsed electromagnetic field ("PEMF") in guinea pigs and found that significantly increased both the rate and final amount of orthodontic tooth movement observed over the 10-day experimental period. Thus, it has been shown that PEMF can be used in place of pulsed micro-currents, a result which is not surprising given that electromagnetic fields can induce current and vice versa.

In 1993, Rubin et al. showed in an in vivo model of osteopenia that the bone resorption that normally parallels disuse can be prevented or even reversed by the exogenous induction of electric fields. Importantly, the manner of the response (i.e., formation, turnover, resorption) was exceedingly sensitive to subtle changes in electric field parameters. Fields below 10 microV/cm, when induced at frequencies between 50 and 150 Hz for 1 hour/day, were sufficient to maintain bone mass even in the absence of function. Reducing the frequency to 15 Hz made the field extremely osteogenic. Indeed, this frequency-specific sinusoidal field initiated more new bone formation than a more complex pulsed electromagnetic field (PEMF), though inducing only 0.1% of the electrical energy of the PEMF. The frequencies and field intensities most effective in the exogenous stimulation of bone formation were similar to those produced by normal functional activity.

Researchers have attempted to develop a device to implement the Davidovitch micropulse method. U.S. Pat. No. 4,153,060 by Korostoff and Davidovitch, for example, describes an intraoral device wherein an anodic electrode is placed in the direction of applied force and a cathodic electronic on the opposite side of the tooth to be moved. However, being completely intraoral, complex and requiring semi-permanent attachment of electrodes, the device was impractical and never commercialized.

U.S. Pat. No. 4,854,865 was another attempt to capitalize on the Davidovitch research and develop a device suitable for orthodontic electro-osteogenesis. Another completely intraoral device is described in this patent, having an anode that is positioned against the epithelial gingiva, whilst a cathode is placed in engagement with epithelial gingiva at a position adjacent to the tooth to be repositioned, and electric current is applied between the cathode and anode. The device uses noble metals for both electrodes, and an electrolytic gel provides good conduction. This device is also less than practical, both because it targets one tooth at a time, but also because it placed the electricity generating portion of the device inside the mouth, which has limited room and raises the potential of shorts or leaks, and the resulting unpleasant consequences.

US20100082027 describes the use of microcurrent therapy to control oral inflammation where the frequency is 0.1-970 Hz and the amplitude from 20-400 microAmps. Although having a very different purpose, a device is described with external electrical pulse generator coupled to leads that attach to a patient's head and inside the patient's mouth. Therefore, this device is impractical or inappropriate for dental remodeling uses.

Thus, what are needed in the art are practical and safe devices that allow the safe and comfortable use of electro-osteogenesis to speed orthodontic remodeling.

SUMMARY OF THE INVENTION

The device described herein capitalizes on the special bite plate developed by OrthoAccel for the AcceleDent product line, but combines the bite plate with electrodes that can generate a micro-pulsed current or electromagnetic (EM) field to the teeth and/or periodontal tissue.

Depending on which teeth or regions of dentition that need to be treated, different dental plate shapes are possible. However, the dental plate is generally flat to allow contact of the occlusal surfaces of all teeth, or at least three points thereof, and U-shaped. Alternatively, the dental plate may cover only a portion of the dentition, thus being restricted to fewer teeth in use and differential tooth movement as a planned treatment approach.

The dental plate also has one or more vertical edges or phalanges (perpendicular to the midline when positioned inside the mouth), said edges being positioned to contact the facial and/or lingual surfaces of the teeth and typically even apically beyond the gum line. In preferred embodiments, the dental plate has a U-shaped bite plate, and is slightly tapered to be thinner in the back of the mouth to accommodate the hinged nature of the jaw structure.

Custom designed bite plates can also be made, wherein the anodic electrode is placed in the direction of applied force and a cathodic electrode on the opposite side of the tooth to be moved. However, it is expected that a universal bite plate will be more cost effective, although with 3D printing technology, custom bite plates may become more practical in the near future as 3D technology costs decrease.

Even with a universal bite plate, teeth that are severely out of plane can be contacted with the use of inexpensive peel and stick risers or buttons, attached for example to the occlusal surface of the bite plate so as to contact a recessed tooth. Alternatively, the bite plate can be combined with a bead of light curable resin, as described in 61/701,532, although care needs to be taken not to block the electrodes or to use a conducting resin. Contact with all teeth can be important, for example in a combination vibration and micro-pulse device, but contact with all teeth may not be essential for the pure micro-pulse device, especially since teeth conduct electricity.

The electrodes are preferably thin wires or strips, e.g., made of platinum or gold or other conductive material, and are printed or otherwise laid on those surfaces of the bite plate that contact the teeth and/or gums, and operably connected to a current generator that is provided inside an extraoral housing, along with all of the other components needed to make the device work. Where an electromagnetic field is used, the electrodes may also be coiled.

The electrodes can be patterned such that the cathode is adjacent to the lingual surfaces and the anode to the facial surfaces, or vice versa, but preferably, the cathodes are positioned against the gingiva and the anodes against the teeth, or vice versa, as this design does not require a electrical connection through the teeth, but rather provides a tiny current on one side of the teeth. The entirety of say, the upper gingiva can thus be in contact with the cathodes and the upper teeth in contact with the anodes.

Alternatively, separate electrodes can be provided for each tooth, or a small group of teeth, allowing very specific electric fields to be applied as needed on a tooth-by-tooth or quadrant basis. However, a single electrode is preferred as minimizing the wires and connections and thus much simpler to build, having a smaller footprint, and being more robust. Thus, with 4 cathodes and 4 anodes, every tooth surface can be contacted. If preferred, only one of the lingual or facial surfaces of the teeth and periodontal tissue can be treated, thus requiring only 4 electrodes, instead of 8.

Preferably, a custom or semi-custom application-specific integrated circuit (ASIC) is designed to drive the device, and is particularly preferred for a completely intraoral device. An ASIC can include entire microprocessors, memory blocks including ROM, RAM, EEPROM, Flash and other large building blocks. Such an ASIC is often termed a SoC (system-on-chip). Hardware description language (HDL), such as Verilog or VHDL, can be used to describe the functionality of ASICs. Field-programmable gate arrays (FPGA) are another option for driving the device. Programmable logic blocks and programmable interconnects allow the same FPGA to be used in many different applications. For smaller designs and/or lower production volumes, FPGAs may be more cost effective than an ASIC design even in production.

Another option is to use structured ASIC design (also referred to as "platform ASIC design"), because both manufacturing cycle time and design cycle time are reduced compared to cell-based ASIC, by virtue of there being pre-defined metal layers (thus reducing manufacturing time) and pre-characterization of what is on the silicon (thus reducing design cycle time). Design differentiation and customization is achieved by creating custom metal layers that create custom connections between predefined lower-layer logic elements. "Structured ASIC" technology is seen as bridging the gap between field-programmable gate arrays and "standard-cell" ASIC designs. Because only a small number of chip layers must be custom-produced, "structured ASIC" designs have much smaller non-recurring expenditures than "standard-cell" or "full-custom" chips, which require that a full mask set be produced for every design.

In one custom embodiment of the electro-orthodontic device, the bite plate is in effect an aligner, custom fitted for each patient, and applies both corrective forces, as well as providing electrical stimulation. For an aligner-type embodiment, the device should be completely intraoral and use either small batteries or charged capacitors. The batteries or charged capacitor, etc. are hidden on the lingual side or behind facial surfaces (behind the cheek), or underneath the tongue or in the palate (roof of the mouth). As another alternative, a wirelessly rechargeable battery is used in such an embodiment, and the device is hermetically sealed. The aligner embodiment can be built as an integrated device, or peel and stick strips containing the electrodes, processor and power source can be applied to existing aligners.

In one preferred embodiment, the current/EM generating device is combined with a vibrational device, thus speeding dental remodeling in two different ways, and it is anticipated that the combination of the two will prove to be synergistic. In this embodiment, the power and processor are preferably extra-oral, to minimize bulk inside the mouth, maximize safety and reduce regulatory hurdles, although intra-oral devices can be designed.

In another embodiment, pulsed electromagnetic fields are used to generate a local micro-current. This method may be preferred by patients and present fewer regulatory hurdles. Electrodes for a pulsed electromagnetic field can be placed inside the biocompatible coating on the bite plate, since the EM field can pass through the polymer. When a PEMF device is to be used, the electrodes may be coiled.

A useful frequency range is approximately 0.1 Hz. to approximately 100 Hz. Lower frequencies appear to be more efficacious than higher frequencies, thus, the preferred frequency is 1-25 Hz or less, or most preferred about 10-20 or 15 Hz. A current density less than 0.1-100 µAmp is a useful current range. Results in the literature as to what the best amperage may vary, ranging from 1-10 $\mu Amp/mm^2$, and the most efficacious amperage may depending upon the number of teeth to be repositioned, the size and relative density of the epithelial gingiva, as well as other factors. Experiments will need to confirm which voltage/frequency is best and the answer may vary depending on whether an electrolyte gel is used with the device, and on the exact patterning of electrodes employed. It is expected that the lowest efficacious current density will be selected as providing for efficacy, safety, and patient comfort.

The wave form can be square or sinusoidal or of any other form. Experiments will need to confirm which wave form is the best, but this information is not yet available.

Where a PEMF is used, suitable field strength would be 1-100 mTesla, and a frequency of 0-1000 Hz, preferably 0.1-1 mT and 1-150 Hz, although at least one paper reports positive results with 72 mT and 50 Hz. The ideal frequency and strength for orthodontic use have yet to be conclusively determined, however.

The bite plate is shaped to contact the teeth at any point or all points, but preferably contacts occlusal surfaces and lingual or facial (preferably both) surfaces of the teeth, although specialty plates can be designed for serious clinical abnormalities. Thus, the bite plate is generally U-shaped and has rims or phalanges on inner and/or outer edges of the U, which serves to contact lingual and/or facial teeth and gum surfaces on both upper and lower teeth.

Generally, the bite plate has a stiff inner core, which provides the needed structural stability for connection to the extra-oral housing, which contains the battery, processor and the like. In the case where vibrational force is combined with electrical current, the stiff inner core is also capable of transmitting the vibrational force from the extraoral vibrator to the teeth. The core is usually coated with a biocompatible polymer, such as medical grade silicon, for patient comfort, but this is not essential, and the bite plate can comprise just the core material.

Preferably the inner core is the same as existing cores, e.g., as described in US2010055634 because use of the same inner core and connector will allow many of the existing device parts to be used, including core, connector, housing, and the like.

Core material can be any resin, ceramic, glass or metal, but resin is preferred as cost effective and moldable. Suitable plastics include polyethylene, polypropylene, polybutadiene, polycarbonate, polyvinylchloride, polymethylmethacrylate, and the like.

Other resins include high density polyethylene plastic (HDPE), ultra high molecular weight polyethylene plastic (UHMWPE), MC cast nylon 6/66 plastic (Nylon), polytetrafluoroethylene plastic (PTFE/Teflon), acrylonitrile butadiene styrene (ABS), polyamides (PA), polybutylene terephthalate (PBT), polyethylene terephthalate (PET), polyphenylene oxide (PPO), polysulphone (PSU), polyetherketone (PEK), polyetheretherketone (PEEK), polyimides, and polyoxymethylene plastic (POM/Acetal).

Coatings, such as silicone rubber, polyurethanes, polycarbonate, cellulosics, styrene butadiene copolymers, are available in clear medical grade resins, but many more such resins may be available. Preferably, the coating will not have an objectionable taste and will be Food and Drug Administration (FDA) approved or cleared, such as medical grade silicone rubber, and the like.

In yet another embodiment, the device is coated with a polymer that can be reshaped for custom fit, such as boil and bite polymers, or polymers that can be activated, cured, and/or set with the addition of light and/or chemicals.

The electrodes for current production are patterned on the biocompatible polymeric coating of the bite plate, but can be inside the coating where an EM field is used, or can be inside if the polymeric coating sufficiently conducts electricity. Electrically conducting films are known, such as conjugated polymers like polyacetylene, or a conducting additive can be added thereto, such as 2% polyaniline (PANI), metals or graphite, and the like. Alternatively, the electrodes can be printed on the bite plate and a conductive film laid thereover, thus allowing current, but providing a protective layer for the electrodes, and retaining the comfort of the biocompatible coating.

Any suitable electrode material can be used, including metals, silicone, conductive plastics, conductive carbon forms, and the like. Metals such as the noble and precious metals are preferred, but gold may be particularly preferred, as it is known to be biologically inert. The noble metals are metals that are resistant to corrosion and oxidation in moist air, unlike most base metals, and are considered to include ruthenium, rhodium, palladium, silver, osmium, iridium, platinum, and gold, and some sources include mercury or even rhenium as a noble metal. On the other hand, titanium, niobium, and tantalum are not included as noble metals despite the fact that they are very resistant to corrosion. The precious metals include gold, silver, platinum, and palladium. Other precious metals include the platinum group metals: ruthenium, rhodium, palladium, osmium, iridium, and platinum.

In another preferred embodiment, the electrode itself is a conducting polymer, laid or printed on the surface of the bite plate. Many conducting plastics are available, for example PEDOT-poly(3,4-ethylenedioxythiophene), metal impregnated polymers, graphite impregnated polymers, conjugated polymers, and the like. Carbon-based screen-printed electrodes (SPCEs), conductive graphene films are also available, as are other biocompatible electrode materials.

Generally speaking, the housing is waterproof, or hermetically sealed, or at least water resistant, and encloses a battery and a processor, as well the wiring and software instructions needed to operate same. The processor thus controls the micro-pulsed electric or magnetic fields. Where a vibrator is included, the processor can also control the vibrator, which is also preferably housed in the extra-oral housing.

The processor preferably also runs software that captures usage frequency, amperage, voltage, duration, and the like, and can be programmed to change the frequency, wave form, voltage, amperage, duration, force, or any other operating parameter. As discussed above, a custom, semi-custom or structure ASIC design is preferably used to drive the device.

The processor can communicate usage frequency and duration to a remote computer via any type of wired or wireless communication method, e.g., a USB port. The processor can communicate with the remote computer over the Internet, via smartphone, etc. The processor can also actively communicate with the user to provide input related to device use, e.g., related to biting too hard on the bite plate or alerting the user when optimal usage period is complete.

A mechanism can be provided to measure proper use based on moisture or temperature sensing, or salivary mineral content sensing, and feedback can be provided based on this control parameter as well. Indeed, the electrodes themselves can function as moisture sensors, since the device can be designed so that current will not flow in a dry condition. This is a very helpful feature for monitoring usage in young patients, because the patient, as an example of contrived non-compliance, cannot just turn it on for 10 minutes, or some other lesser period of time, and leave it on the countertop or elsewhere, as this approach will not be recorded as correct usage.

The device can be wired and plugged in for power, but preferably uses a non-rechargeable or rechargeable battery to drive it. This is both safer and allows the user more mobility. The rechargeable battery can be charged using power from any type of power source including via a USB port or an RS-232 port or a FireWire port, for example, or a dedicated docking/charging station can be provided. Disposable batteries may also drive the vibrational source, especially for intraoral embodiments. Small coin batteries, alkaline or lithium, are preferred due to their small size, but hydrogen batteries may also be preferred due to their power and power density, particularly as size and cost decrease with further technological development.

For certain embodiments, especially intraoral embodiments, a battery that can be wirelessly recharged is preferred for longer product life (e.g., US20090051312, U.S. Pat. No. 7,511,454) and for safety reasons, but in other embodiments a low cost device is manufactured that is intended to be disposable, and coin batteries are thus preferred.

In other embodiments, such as when combined with an aligner, a charged capacitor can be used, because the aligners are intended for use for only a few days, and then the patient is provided with a new aligner. Thus, a very limited life span is needed in this embodiment. Any charged capacitor construction can be used, including a parallel plate capacitor, or multiple plates connected in series.

Any off the shelf on/off switch can be used. Particularly preferred for the intraoral device is an on/off switch with depressible activator (push button, rocker or membrane button). Membrane buttons are particularly preferred as watertight and of pleasant tactile feel.

If vibration is to be combined with a micro-pulse modality, there are many options available. Vibration is most commonly provided via a motor that rotates a shaft having an unbalanced or eccentric weight (off-set motor) or a piezoelectric based device, but any other vibrating means can be used. The known methods of producing vibration include motor and camshaft, motor and linkage, motor rack and pinion, motor and drive belt, and similar mechanical methods. However, solenoid vibrators, linear coil vibrators, linear resonance actuators, voice coil actuators, and the like can also be used. Existing commercial vibration motors include long life brushless (BLDC) vibration motors, coin A large number of very small motors are commercially available, as shown in the table below, but piezoelectric motors may be preferred due to the small size, although off-set weighted motors may be preferred due to low cost and availability. Particularly preferred are the substantially planar motors where the vibration is substantially parallel to the substrate (e.g., U.S. Pat. No. 5,554,971, U.S. Pat. No. 5,780,958, US20090224616, US20080129130, US20070103016, WO0178217, each incorporated by reference).

| Company | Catalog | Size | Specifications |
|---|---|---|---|
| ELLIPTEC AG ™ | NA See U.S. Pat. No. 6,870,304 | 10 × 3 × 2 mm | 3-6 volts piezoelectric motor |
| SURPLUS TRADERS ™ | MF820 | 8 × 4 mm (0.315 × 0.1575 inches) | 1.5 to 4.5 VDC weighted shaft |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |
| SURPLUS TRADERS ™ | MF835 | 0.45 × 0.24 inches | 1.3 Vdc 100 mA Weighted shaft |
| MATSUSHITA ™ | V0296A | 0.24 inch diameter | 1.5 VDC Weighted shaft |
| SURPLUS TRADERS ™ | ME235 | 0.24 × 0.5 inches | 1.5 to 3 VDC 62 mA weighted shaft |
| PRECISION MICRODRIVES ™ | 304-002 | 4 m × 8 mm | 2.3 VDC to 3.6 VDC 100-120 mA 11000 rpm Weighted shaft |
| PRECISION MICRODRIVES ™ | 308-100 | 3.4 × 8 | 2.-3.3 V, 120 mA 12000 rpm 8 mm Shaftless Vibration Motor |

(pancake) vibration motors, encapsulated vibration motors, pager motors, PCB mounted vibration motors, coreless DC motors, ultrasonic motors, to name but a few.

Consistency of frequency and force can be achieved herein via a feedback loop whereby motor speed is monitored and software adjusts the motor as needed. More particularly, the motor contains an integrated encoder that provides multiple high and low signal outputs per every motor revolution. The software counts the time between every encoder event (e.g., a rotating disc with markings thereon can be optically sensed) and compares this to the desired target (e.g., 30 Hz). Based on this comparison, the software then adjusts the pulse width modulation that is driving the motor to increase or decrease speed as appropriate to maintain the desired speed. Accurate controlling of speed also controls the force.

Integrated optical encoders may be preferred, as one type of rotary encoder, but the feedback mechanism can be any known technology. Encoders can be separate or integrated, and be optical, magnetic, or capacitive encoders. A proportional-integral-derivative controller (PID controller) is another option. The PID is a generic control loop feedback mechanism widely used in industrial control systems.

The same motors become non-vibratory if no off-set weight is included thereon. The ideal motor would be thus be quiet and combinable with a feedback mechanism to precisely control the motor. Further, it would be small, have a good working life at a cost effective price.

Vibrations may be oscillating, random, directional, circular, and the like. Vibrators are well within the skill of the art, and several are described in the patent literature (and commercially available as seen above). For example, US20070299372, US20070255188, US20070208284, US20070179414, US20070161931, US20070161461, US20060287620, each incorporated by reference, describes various vibrating motors.

The device can be used alone, but is preferably used in combination with other orthodontic devices, such as braces, aligners, and the like, which provide the orthodontic forces need to move teeth to a desired position. In some embodiments, the appliance can be used to speed boney remodeling in orthodontic uses with traditional orthodontic fixed appliances or aligner based treatments or any other appliance used for tooth movement. In other embodiments the appliance can be used alone to enhance boney remodeling in periodontal and oral surgical uses.

The electric current or PEMF devices of the invention can also be combined with other stimuli, such as infrared light, heat, and vibration, as already discussed above. In such embodiments, the device is simply fitted with e.g., a light source, heat source, or vibrational source, as disclosed in 61/624,242, US20080227046, and US20100055634, each incorporated by reference.

The device of the invention can be used in a variety of oral and maxillofacial applications including malocclusion, trauma repair, temporomandibular joint and muscle disorders (TMJDs), Lefort and other skeletal facial fractures, craniofacial anomalies such as boney clefts, bone defects, dentofacial deformities, dental implants, periodontal bone grafts as well as tooth, muscle, nerve, tendon, ligament, bone, and connective tissue repair.

In use, the bite plate is placed into the patient's mouth, and the patient holds the device by biting down on the bite plate. No other attachment means are needed, and this greatly improve patient acceptance of the device over the prior art bulky headgear or semi-permanent electrode attachment devices. The device is activated and micro-current applied for at least 5-30 minutes daily, preferably 10-20 minutes at least once a day, or 2-4× per day.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated. In the context of specific dimensions of parts, the term "about" includes that amount of tolerance that still allows the parts to operably fit together. Tolerances may be somewhat higher for flexible materials, e.g., silicone rubbers, than for harder materials, e.g., metals.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim.

The phrase "consisting of" is closed, and excludes all additional elements.

The phrase "consisting essentially of" excludes additional material elements, such as bulky headgear for attachment, toothbrush bristles, and other modes of action, but allows the inclusions of non-material elements that do not substantially change the micro-pulse nature of the invention, such as additional indicator lights, instructions for use, labels, control buttons or dials, and the like.

DESCRIPTION OF EMBODIMENTS

The disclosure provides a novel electro-orthodontic remodeling device having a special bite plate that contacts lingual and facial teeth surfaces, in addition to occlusal surfaces, and has electrodes thereon for provide current or EM fields to the teeth and/or periodontal tissue.

The invention can comprise one or more of the following embodiments, in any combination:

An electro-orthodontic remodeling device comprising: an intraoral bite plate having a substantially U-shaped surface for contacting an occlusal surface of teeth; said U-shaped bite plate having an outside edge having upper and lower rims to contact upper and lower facial surfaces of teeth and gums; said upper and lower rims having anodes and cathodes on tooth and gum contacting surfaces thereof; an extraoral waterproof housing containing a power source operably coupled to a processor for controlling said voltage source and providing said anodes and cathodes with either: a current of less than 100 μAmp at a frequency of less than 100 Hz, or a pulsed magnetic field of less than 100 mTesla at 0-150 Hz; wherein said U-shaped bite plate reversibly and operably connects to said housing; wherein said device is held in place during usage by teeth clamping on the bite plate and lacks any head or neck attachment devices.

An electro-orthodontic remodeling device comprising: a flexible strip have a first side and a second side, said strip having an adhesive coating on said first side, said adhesive coating covered with a removable protective layer, one or more pair of electrodes on said second side, said electrodes electrically connected to a voltage source and an on/off switch on said strip, said voltage source being able to provide a current of ≤100 micro-Amp at ≤100 Hz to said electrodes or an electromagnetic field of ≤100 mTesla at ≤150 Hz from said electrodes.

A completely intra-oral electro-orthodontic device, comprising: an intraoral bite plate allowing for contact with an occlusal surface and at least one of lingual and buccal surfaces of upper and lower teeth and gums, and wherein a surface of said bite plate has two or more electrodes thereon positioned so as to contact said upper and lower tooth and gums when in use; said intraoral bite plate also having a voltage source operably coupled to a processors for controlling said voltage source; said voltage source operably coupled to said electrodes; wherein said processor and voltage source can provide current of less than 100 μAmp at 0-100 Hz to said electrodes or an electromagnetic field of 1-100 mTesla at 0-150 Hz from said electrodes.

An electro-orthodontic remodeling device comprising: an intraoral bite plate having a substantially U-shaped surface for contacting an occlusal surface of teeth, said U-shaped bite plate having an outside edge having upper and lower rims to contact an upper and lower facial surfaces of teeth and gums; said U-shaped bite plate having an inside edge having optional upper and lower rims to contact at least a portion of an upper and lower lingual surfaces of teeth and gums; said upper and lower rims of said outside and optionally inside edges having anodes and cathodes on a tooth and gum contacting surface thereof; an extraoral waterproof housing containing a power source operably coupled to a processor for capturing usage data and for providing current of less than 100 μAmp at a frequency of less than 100 Hz to said anodes and cathodes; said U-shaped bite reversibly and operably connected to said housing; wherein said device is held in place during usage by teeth clamping on the bite plate and lacks other head attachment means.

An electro-orthodontic remodeling device consisting essentially of an intraoral bite plate having a substantially U-shaped surface for contacting an occlusal surface of teeth, said U-shaped bite plate having an outside edge having upper and lower rims to contact an upper and lower facial surfaces of teeth and gums, and said upper and lower rims having electrodes on a surface thereof; said U-shaped bite plate having an inside edge having optional upper and lower rims to contact at least a portion of an upper and lower lingual surfaces of teeth and gums, one or both of said upper and lower rims having positive and negative electrodes on a tooth facing surface thereof; an extraoral waterproof housing containing a charging port operably coupled to a rechargeable battery operably coupled to a processor operably coupled to a data port; said U shape bite plate reversibly and operably connected to said housing; said battery and processor providing a current to said electrodes of less than 100 μAmp or a magnetic field of less than 100 mTesla at 0-150 Hz. This device can also be optionally provided with a vibration source, as herein described.

An electro-orthodontic device, consisting essentially of an extra-oral voltage source; an extra-oral processor operably coupled to an extra-oral data port, wherein said processor controls said extraoral voltage source and captures usage frequency and duration; an extra-oral power source that drives said voltage source and processor; an intraoral attachment consisting of a bite plate allowing for contact with an occlusal surface and at least one of lingual and buccal surfaces of a patient's teeth, wherein a patient biting on said bite plate holds said device in place during use, and wherein a surface of said bite plate has one or more electrodes thereon positioned so as to contact a patients tooth and/or gums when in use; wherein the extraoral voltage source is operably coupled to said pair of electrodes; wherein said orthodontic device is hermetically sealed and can provide current of less than 100 μAmp at 0-100 Hz to said electrodes or an electromagnetic field of 1-100 mTesla at 0-150 Hz from said electrodes.

An electro-orthodontic remodeling device comprising: an intra-oral bite plate having a substantially U-shaped surface for contacting an occlusal surface of teeth, said U-shaped bite plate having an outside edge having upper and lower rims to contact an upper and lower facial surfaces of teeth and gums, and said upper and lower rims having positive and negative electrodes on a tooth contacting surface thereof; said U-shaped bite plate having an inside edge having optional upper and lower rims to contact at least a portion of an upper and lower lingual surfaces of teeth and gums, said upper and lower rims optionally having positive and negative electrodes on a tooth facing surface thereof; said extraoral waterproof housing containing a charging port operably coupled to a rechargeable battery operably coupled to a processor operably coupled to a data port; said electrodes comprising a conductive plastic; said U shape bite plate reversibly and operably connected to said housing; said power source and processor providing a current to said electrodes of less than 100 μAmp or a magnetic field of less than 100 mTesla at 0-150 Hz.

An electro-orthodontic remodeling device comprising: a transparent aligner fitting over a patient's teeth and applying pressure to one or more maloccluded teeth so as to remodel said maloccluded teeth; said aligner having an inner surface that contacts the surface of said patient's teeth and/or gums; said inner surface having a pair of electrodes thereon; said aligner also having an application specific integrated circuit (ASIC) operatively connected to a power source and said electrodes, such that said ASIC provides a current to said electrodes of less than 100 μAmp or a magnetic field of less than 100 mTesla at 0-150 Hz.

The device can also be combined with vibration, preferably at 20-40 Hz, or 30 Hz, and 0.1-0.5N or 0.2-0.25 N. Preferably, the device is also smooth and quiet, having a noise level less than 55 dB when measured at 6 inches, and being capable of vibrating at a frequency of 20-40 Hz, with a variance of only 2 Hz or less, and a force of 0.1-0.5 Newtons, with a variance of +−0.05 N or less.

The processor can store usage data and coding sufficient to convert said usage data into daily use, average daily use and average weekly or monthly use, or convert said usage data into a graphic representation of daily use, average daily use and average weekly or monthly use.

Also provided are methods of orthodontic remodeling, comprising biting the bite plate herein described, or by applying the strip herein described to teeth or a positioner or aligner, and activating said device for at least 10 minutes at least once a day, preferably 20 minutes.

Figure 1:
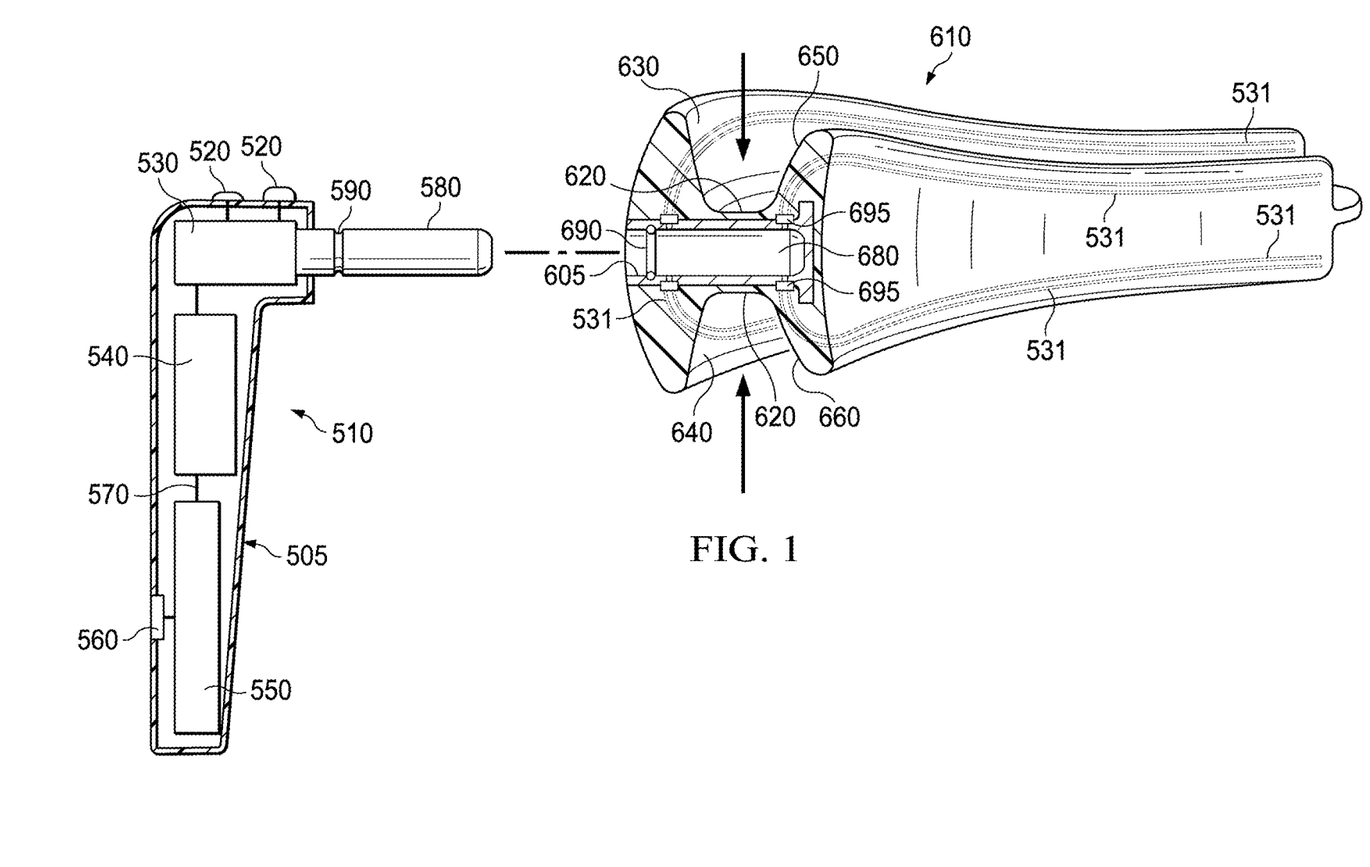
FIG. 1. A bite plate with electrodes reversibly coupled to a watertight extraoral housing that contains all the mechanics and electronics for operating the bite plate.

FIG. 1 is a cross section of the electro-orthodontic driver 510 and half of a bite plate 610. The electro-orthodontic driver 510 has a housing 505 containing all components, except the stem 580, which protrudes therefrom. Preferably, housing 505 is water resistant or even more preferred it is waterproof or hermetically sealed. A voltage and/or EM source 530 is shown schematically as a simple box. The housing also contains power source 540, preferably a rechargeable battery, and can have an optional charging port (either not shown or can be USB port 560).

Processor 550 captures usage data, and may also control the voltage source 530. Data is transmitted to a server or computer or the internet via data port or USB 560, which can also provide for battery recharging. Connections or wires 570 are shown in simple form only and not intended to convey actual wiring connections, as are on/off switches 520.

The voltage source 530 may be the same as battery 540 in some embodiments, but this is not necessarily the case, and in many cases a separate component is needed to interface between the battery and the electrodes, e.g., step up or step down converters, DC to DC converter, DC to AC converter, rectifiers, inverters, and the like.

Stem 580 is shown here with depressions 590, which can circumnavigate the stem in one embodiment, but many variations of snap fitting and other connectors are possible. In addition, the stem can be on the bite plate, and the socket can be in the housing. It is preferred that the bite plate be detachable, as this allows the user to change bite plates, which may become worn, or which may no longer fit as treatment progresses.

Bite plate 610 has a hard inner core that forms the socket 605 and can be any suitable shape. An exemplary circle spring 690 fits into depressions 590 on stem 580 and the bite plate thus removably snap fits onto the extraoral driver 510, but any reversible attachment means or snap-fit means can be used.

The bite plate has the labial, lingual edges and occlusal surfaces. Thus, 620 are the flat surfaces that contacts occlusal surfaces of the teeth, which fit into the bite plate at the heavy arrows. Anterior vertical surfaces 630 and 640 contact the facial tooth surfaces, while posterior vertical surfaces 650 and 660 contact the lingual tooth surfaces.

The core partially inside the lingual phalanges 650 and 660 is shown, but this element can be optional depending on the flexibility of the coating, so if less flexible material is used, the core may not be needed, as shown with facial phalanges 630 and 640, although using a core that fits into the phalanges may simplify manufacturing, as it provides an assembly surface. By "phalange" what is meant herein is the vertical edges or rims on the U-shaped bite plate.

The various teeth contacting surfaces of the bite plate can be shaped to closely follow a patient's teeth, as with an aligner, or can be simplified and fit a wide range of dentition and allow use over traditional braces. Preferably, these edges or coating is made of a resilient material of durometer at least 30-80 Shore A, most preferred is a biocompatible or medical grade clear silicone of about 40 Shore A.

The surfaces of the bite plate have electrodes 531 which can be placed on the core or on the coating if present, and can optionally be covered with a film of conductive resin. Electrodes 531 can be any suitable distance apart, but are preferably from 2-10 mm apart, ~7 mm, and either electrode can be the anode or cathode.

Figure 2:
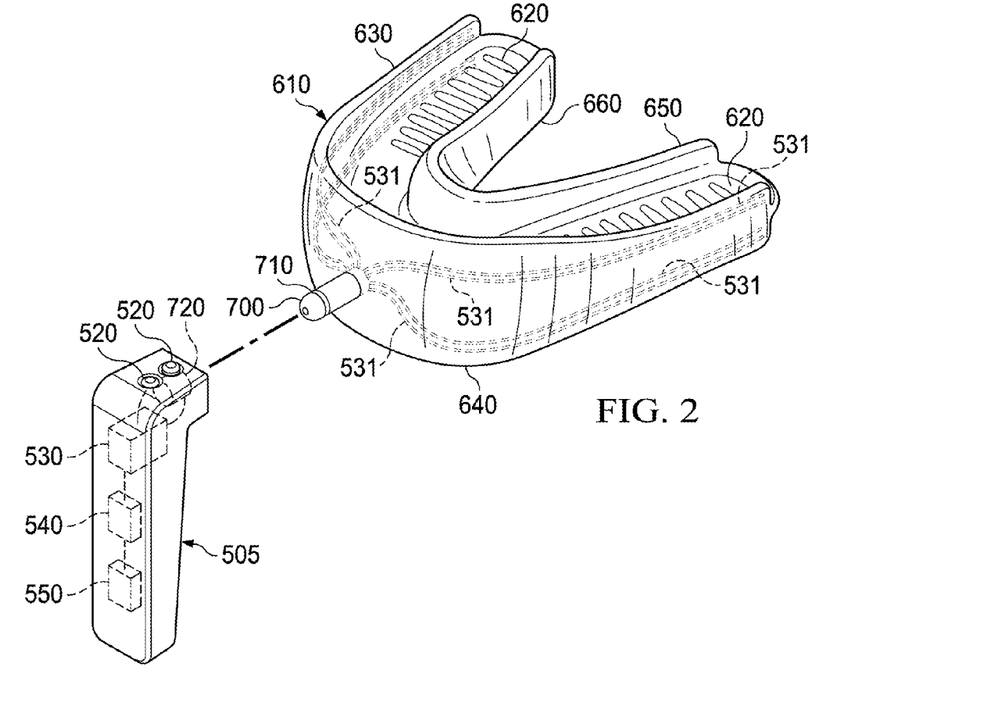
FIG. 2. Another embodiment of a bite plate with electrodes.

In this simple figure, the electrodes are shown connecting to the stem on the sides of the stem, and the requisite connectors 695 shown as small boxes, and the interior wiring inside the stem is not shown. Another configuration is shown in FIG. 2, wherein the electrodes are shown terminated with a connector inside a stem 700 with depression 710 that fits into a socket 720 on the housing having protrusions (not shown) to snap fit into depressions 710.

In this embodiment, the electrodes only contact the facial surface of the teeth and/or gum, and there are no electrodes on the lingual side, and this may be preferred as the tongue is expected have increased sensitivity to current. However, there are still 4 pairs of electrodes, thus shortening the distance the current needs to travel and reducing losses. Alternatively, a single wire can bifurcate, covering both sides of the oral cavity. Electrode configuration and placement can thus vary.

The processor 550 can be configured to provide a wide range of functionalities, including one or more of 1) recording usage data, 2) transmitting usage data wirelessly or via USB port or other connections, 3) wirelessly transmits data to a smartphone application that reminds the user when to use same and/or reports usage to a parent or dental professional, 4) tuning the frequency and voltage over an acceptable efficacious range, and 5) when combined with a vibrator can allow selection of vibration frequency and force over an acceptable efficacious range.

Figure 3:
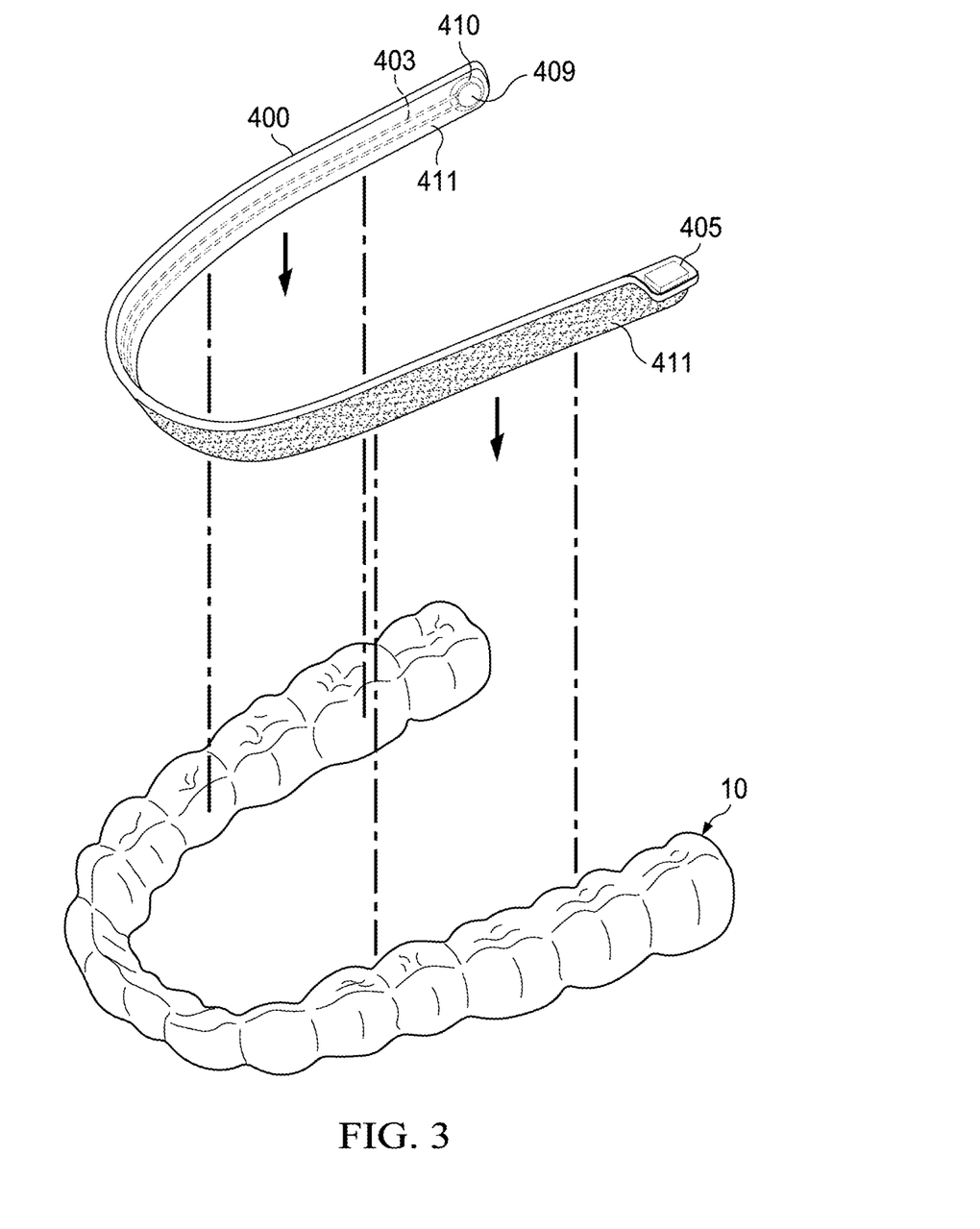
FIG. 3. A peel and stick electro-orthodontic strip.

FIG. 3 shows a peel and stick electrode strip that can be applied to existing aligners, positioners, bite plates, and the like, thus speeding their remodeling effect. This embodiment is a simple, flexible strip 400 having an on/off switch 405 connected to electrodes 403, battery 409 and processor or ASIC 410. Preferable, the strip is flexible enough to allow it to be bent to use with various sized aligners, e.g., 30-70 Shore A and has a smooth lingual surface with a very low profile, and a flat back surface, with adhesive layer 411, and a removable protective layer over the adhesive layer (not shown, but well known in the art).

In the embodiment shown, the on/off switch 405 lies on the occlusal face, such that it can be activated by biting with a molar, but it could also be on a lingual or facial surface and activated with the finger or tongue. Furthermore, the adhesive is shown on the surface opposite the electrodes, but this is optional, and the strip can be configured appropriately for its intended use. An application-specific integrated circuit 410 can be designed to drive the device, allowing it to be completely intraoral and lacking any extra-oral components. Batteries or charged capacitors can be selected to allow several hours of use, and if wirelessly rechargeable batteries are employed, the device should last through an entire treatment period. Alternatively, the device can be cost effective enough to allow disposal when the batteries wear out.

In use, the protective strip is removed, and the electrode strip applied to retainer 10 or other device or even applied directly to the teeth. The attachment can vary. If thin enough, the strip can fit inside the retainer and thus be pushed directly against the teeth. However, it may be preferred to apply the strip to the outer surface of the retainer, such that the electrodes come into contact with the gums, above or below the retainer, and in such embodiment, the adhesive would be on the same side of the electrodes.

We anticipate that such a micropulse strip can be made inexpensively enough that the patient can purchase a dozen or so, to be used with the various aligners made throughout the course of his or her treatment. Once attached, the patient can activate the switch with the tongue, finger or tooth, and apply current to the treatment area for the desired time period, e.g., every few days, daily, or more frequently. In a variation on this theme, it is possible that the strip can be attached magnetically, rather than with adhesive, and thus be removed when not in use. Other attachments means are also possible.

Figure 4:
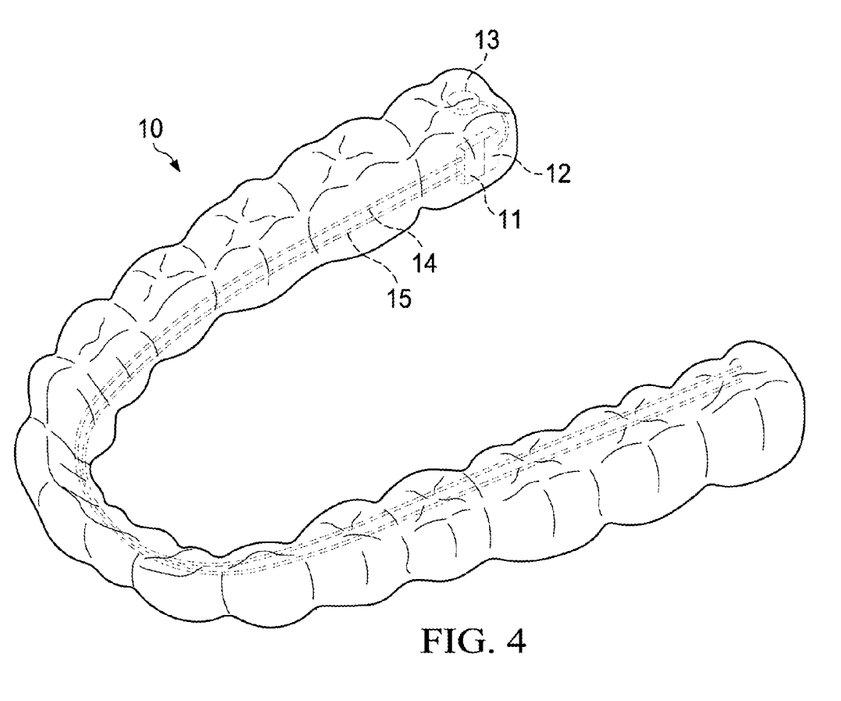
FIG. 4 shows a modified aligner having an ASIC, charged capacitor, one/off button on the molar, and electrodes on an inner surface of the aligner.

FIG. 4 shows alternative custom embodiment, wherein the micro-pulse driver and electrodes are integrated with the aligner during manufacture. Aligner 10 includes an ASIC 11, charged capacitor 12, on/off button 13 positioned to be activated by biting the molars, and electrodes 14 and 15. These electrodes 14 and 15 may be on an inner lingual surface of the aligner (for aesthetics) where they can contact the lingual surfaces of the teeth and/or gums, but the remaining components can be either on an inner lingual surface or an outer lingual surface as desired for low bulk, aesthetics and ease of manufacturing (they are shown on the inner lingual surface herein). The electrodes can also be on a facial surface, particularly where the electrode materials are translucent or do not otherwise interfere with aesthetics. The on/off switch in such embodiment is optional, thus reducing bulk, where the ASIC is designed to provide multiple pulses on e.g., an hourly or bihourly basis. In such embodiment, the micro-pulses are applied whenever the patient utilizes the device. When an on/off switch is included, the aligner provides micro-pulses at the patient's discretion.

Figure 5:
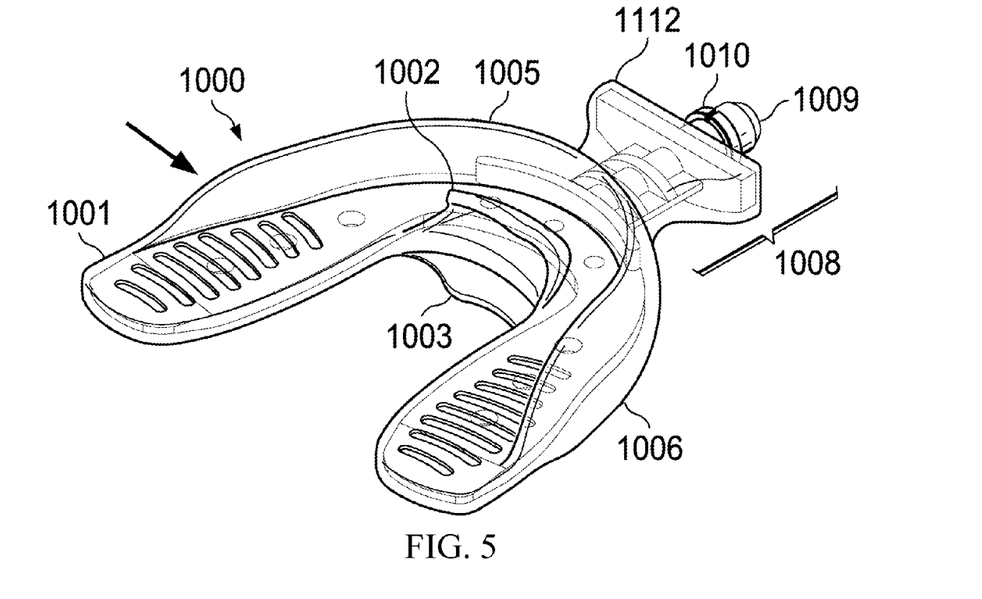
FIG. 5 shows the prior art bite plate with shaped coating and inner core thereof, which can be used to make bite plates that are compatible with the existing inner core and housing by simply adding the electrodes to the bite plate, and appropriate electronics inside the housing. By using the existing inner core and housing and common components, costs and development time can be reduced.

FIG. 5 shows the exterior shape of a bite plate that can include the electrodes as described herein. Bite plate (1000) has a generally U-shaped base (1001) that contacts occlusal surfaces of the teeth, the base having front and back edges, one or both edges having a rim to contact the facial and lingual surfaces of teeth and/or gums. Thus, upper lingual rim (1002), lower lingual rim (1003), upper facial rim (1005) and lower facial rim (1006) are shown. In this instance, the lingual rims contact only the incisors and/or canines, but not the molars. However, the rims can be varied in length to contact all, or a portion, of the teeth. It is preferred that at least one rim contact each tooth, except for badly malocculded teeth, which by definition are out of alignment.

Although the facial rims can contact all teeth, many children lack wisdom teeth, and there is limited space and often distal appliances further reducing space. Thus, the facial rim can taper off distally, as shown. The lingual rim need not contact more than the incisors, since the vibration is already effectively transmitted via the facial rims, and the lingual rims are for device placement and stability in use. Herbst accommodating bite plates can also be used, with facial rims that do not touch the premolars or molars, as described in 61/824,798, filed May 17, 2013.

Also shown is the stem (1008), which is the portion of the bite plate (1000) that mates with a corresponding socket in the extra-oral housing (not shown here), which contains the power source, vibratory source, processor for controlling the mechanism and providing compliance features.

In more detail, a cylindrical shaft 1009 is shown, having a groove into which a jump ring (not shown) fits, and mates with a corresponding depression in the socket. Optional flare (1112) is also shown, and is configured to provide an appropriate surface so that the user can push the stem into the socket.

Figure 6A:
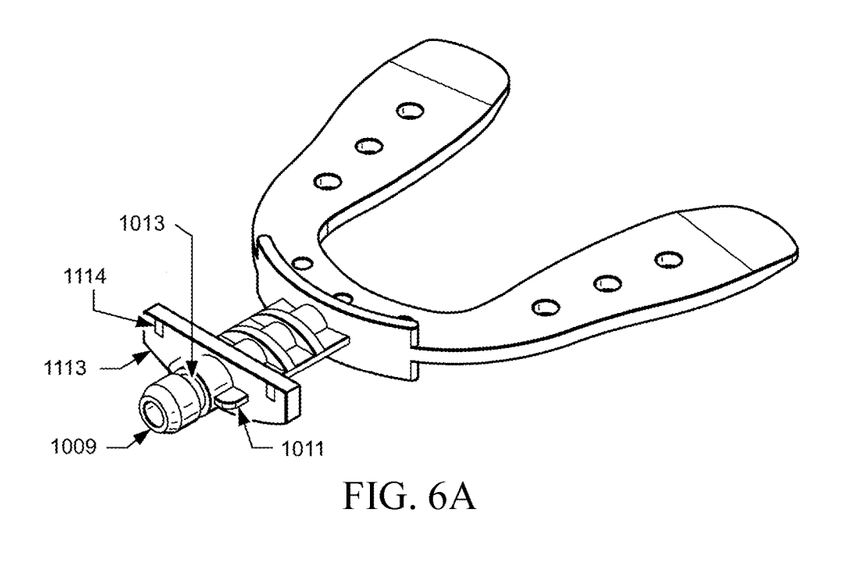
FIG. 6A-D provides the preferred dimensions of the connector.
Figure 6B:
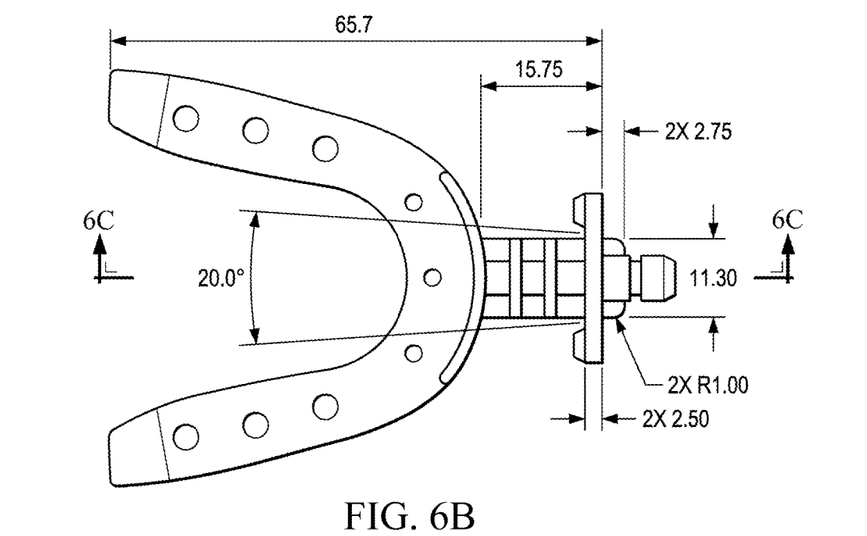
Figure 6C:
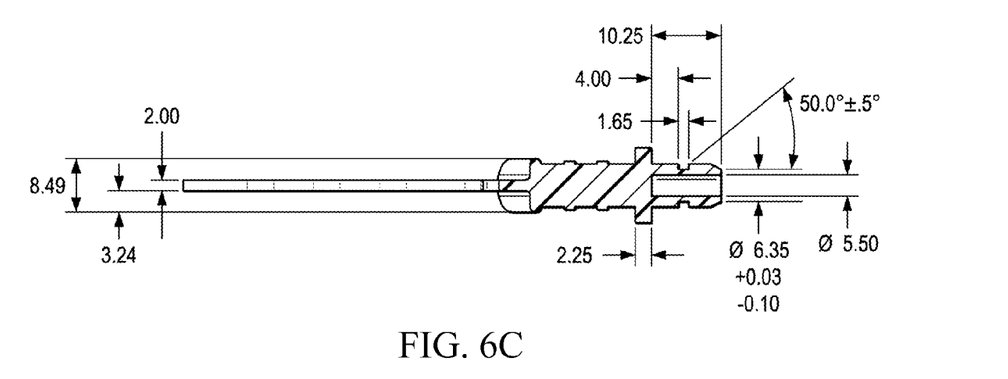

FIGS. 6A-D show the dimensions of the bite plate inner core and connector. Preferably, the connector operably connects (snap fits) into the socket found on the AcceleDent® and AcceleDent® Aura. Using similar connectors allows the bite plates to be interchangeable, and also allows any bite plate inventory to be used even when the driver unit model is updated. Thus, these sizes are valuable for interchangeability of parts. In FIG. 6C, the minimum for interchangeable parts requires the cylindrical post 1009 of about 10.25 mm in length by about 6.35 mm in diameter (tolerance in the diagram noted to be +0.03, −0.1) mm with a groove at about 4 mm from the attached end of the post.

The connector has a flared base (flare not shown herein because made from the over-coating material, but can be seen in FIG. 5 etc.) with a flat surface opposite the bite plate, from which protrudes a centrally positioned cylindrical post that is 6-7 (6.35+0.03, −0.1) mm in diameter, 10-11 (10.25) mm in length, and having a groove circumventing the post about half way (4 mm from flat surface), the groove having a width of 1.65 mm. The flared portion is dumbbell in cross section and provides a suitable surface for the thumb and finger to push the bite plate connector into the socket on the driver.

Figure 6D:
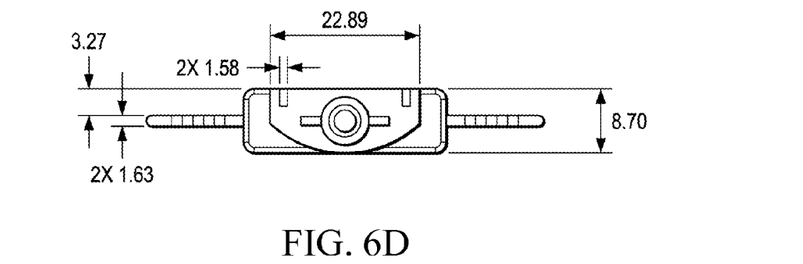

As shown in FIG. 6B, the bottom of the post also has a pair of ~1.4×3 mm pins (optional) projecting 180° from each other (in the same plane as the occlusal contacting base of the bite plate). These pins have a total spread of 11.30 mm at the topmost edge, but flare 10° on each side (20° total) to reach the flat surface of the base. The pins are 1.63 mm thick (as shown in FIG. 6D), and 2.75 mm high (as shown in FIG. 6B).

The base of the connector also preferably has a pair of recessions 1114, which are ~1.5 mm wide×3 mm long×2 mm deep (1.58×3.27×2.5 mm) on the flat surface 1113 thereof for engaging clips from the driver, the recessions 1114 being about 16-17 mm apart (22.89 mm in spread), and positioned right below the pins. The recessions 1114 can be omitted however, if the base is either not flared or is otherwise smaller, such that the remaining post and pins still fit, leaving the engaging clips on the driver free. These dimensions are approximate, and exact dimensions are provided on FIG. 6A-D. Tolerances are as appropriate for the material, while still providing a reversibly locking fit.

The following references are incorporated by reference in their entirety.

60/906,807, US20080227046, US20080227047, US20090051312, US20100055634, 61/624,242, PCT/US13/36289, US20110136070, US20120040300, US20130059263 and US201300322018, Ser. No. 13/850,151, 61/673,236, 61/769,507, 61/701,532, 61/824,798.

Kau, et al., The clinical evaluation of a novel cyclical force generating device in orthodontics, Orthodontic Practice 1(1) (2010).

Davidovitch Z, et al., Electric currents, bone remodeling, and orthodontic tooth movement. II. Increase in rate of tooth movement and periodontal cyclic nucleotide levels by combined force and electric current, Am J Orthod. 77(1):33-47 (1980).

Hashimoto, H., Effect of Micropulsed Electricity on Experimental Tooth Movement, Nihon Kyosei Shika Gakkai Zasshi. 49(4):352-61 (1990).

Rubin C T, Optimization of electric field parameters for the control of bone remodeling: exploitation of an indigenous mechanism for the prevention of osteopenia, J Bone Miner Res. 8 Suppl 2:S573-81 (1993).

Showkatbakhsh R., et al., The effect of pulsed electromagnetic fields on the acceleration of tooth movement, World J Orthod. 11(4):e52-6 (2010).

Stark, T. M., et al., Effect of pulsed electromagnetic fields on orthodontic tooth movement, American Journal of Orthodontics and Dentofacial Orthopedics 91(2): 91-104 (1987).

U.S. Pat. No. 6,684,639, U.S. Pat. No. 6,832,912, U.S. Pat. No. 7,029,276 by Mao.
U.S. Pat. No. 4,153,060
U.S. Pat. No. 4,854,865
U.S. Pat. No. 5,554,971
U.S. Pat. No. 5,780,958
US20070103016
US20080129130
US20090224616
US20100082027
WO0178217

The invention claimed is:

1. An electro-orthodontic remodeling device comprising:
    a) an intraoral bite plate having a substantially U-shaped surface for contacting an occlusal surface of teeth;
    b) said U-shaped bite plate having an outside edge having upper and lower rims to contact upper and lower facial surfaces of teeth and gums;
    c) said upper and lower rims each having a pair of electrodes comprising an anode and a cathode 2-10 mm apart;
    d) an extraoral waterproof housing containing a power source operably coupled to a processor for controlling said power source and providing said anodes and cathodes and thereby said teeth and gums with either:
        i) an electrical current of less than 100 μAmp at a frequency of less than 100 Hz, or
        ii) a pulsed magnetic field of less than 100 mTesla at 0-150 Hz;
    e) wherein said U-shaped bite plate reversibly and operably connects to said housing;
    f) wherein said device is held in place during usage by teeth clamping on the bite plate and lacks any head or neck attachment devices, and wherein usage of said device accelerates orthodontic tooth movement.

2. The electro-orthodontic remodeling device of claim 1, said power source and processor providing electrical current to said anodes and cathodes of ≤10 μAmp at a frequency of ≤20 Hz.

3. The electro-orthodontic remodeling device of claim 1, further comprising a vibrator inside said housing and being operably connected to said battery and said processor, said vibrator being able to vibrate at 20-40 Hz at a force of 0.1-0.5 Newtons and thus vibrating said bite plate when activated.

4. The electro-orthodontic remodeling device of claim 1, wherein said bite plate comprises a rigid inner core and a biocompatible coating.

5. The electro-orthodontic remodeling device of claim 1, wherein said bite plate further comprises a connector protruding from midline thereof for connecting to a socket in said housing, said connector being a cylindrical post having a base end near said bite plate, said cylindrical post being 5.5 mm in diameter and about 10.25 mm in length and having a groove circumnavigating said cylindrical post at 4 mm from said base end.

6. The electro-orthodontic remodeling device of claim 1, wherein said cathodes and anodes comprise a noble or precious metal.

7. The electro-orthodontic remodeling device of claim 1, wherein said cathodes and anodes comprise a conductive plastic.

8. The electro-orthodontic remodeling device of claim 1, said cathodes and anodes being covered with a conductive film.

9. The electro-orthodontic remodeling device of claim 1, wherein said processor also stores and transmits device usage data and coding sufficient to convert said usage data into daily use, average daily use and average weekly or monthly use.

10. A method of orthodontic remodeling, comprising a patient wearing braces or an aligner biting the bite plate of the electro-orthodontic remodeling device of claim 1, and activating said electro-orthodontic remodeling device for at least 10 minutes at least once a day, wherein said method speeds orthodontic remodeling as compared to a similar patient not using said electro-orthodontic remodeling device.

11. The electro-orthodontic remodeling device of claim 1, wherein said cathodes are configured to be positioned against the gums and the anodes against the teeth, or vice versa.

12. The electro-orthodontic remodeling device of claim 1, comprising four total pairs of electrodes, one pair each for an upper right rim, upper left rim, lower right rim and lower left rim.

* * * * *